United States Patent
Burton et al.

(10) Patent No.: US 8,178,726 B2
(45) Date of Patent: May 15, 2012

(54) HIGH FUNCTIONALITY AMINE COMPOUNDS AND USES THEREFOR

(75) Inventors: Bruce L. Burton, Spring, TX (US); Terry L. Renken, Conroe, TX (US)

(73) Assignee: Huntsman Petrochemical LLC, The Woodlands, TX (US)

( * ) Notice: Subject to any disclaimer, the term of this patent is extended or adjusted under 35 U.S.C. 154(b) by 0 days.

(21) Appl. No.: 12/530,896

(22) PCT Filed: Mar. 14, 2008

(86) PCT No.: PCT/US2008/056947
§ 371 (c)(1),
(2), (4) Date: Sep. 11, 2009

(87) PCT Pub. No.: WO2008/112952
PCT Pub. Date: Sep. 18, 2008

(65) Prior Publication Data
US 2010/0069672 A1    Mar. 18, 2010

Related U.S. Application Data

(60) Provisional application No. 60/895,060, filed on Mar. 15, 2007.

(51) Int. Cl.
C07C 217/42 (2006.01)

(52) U.S. Cl. ........ 564/504; 564/505
(58) Field of Classification Search ........ None
See application file for complete search history.

(56) References Cited

U.S. PATENT DOCUMENTS

| | | |
|---|---|---|
| 2,683,730 A | 7/1954 | Seeger et al. |
| 2,950,263 A | 8/1960 | Abbotson et al. |
| 3,012,008 A | 12/1961 | Lister |
| 3,344,162 A | 9/1967 | Rowton |
| 3,346,557 A | 10/1967 | Patton, Jr. et al. |
| 3,362,979 A | 1/1968 | Bentley |
| 3,394,164 A | 7/1968 | McClellan et al. |
| 4,495,081 A | 1/1985 | Vanderhider et al. |
| 4,705,814 A | 11/1987 | Grigsby, Jr. et al. |
| 4,748,192 A | 5/1988 | Smith |
| 5,103,062 A | 4/1992 | Cuscurida et al. |
| 6,960,625 B2 | 11/2005 | Christenson et al. |
| 2005/0234216 A1 | 10/2005 | Klein et al. |

OTHER PUBLICATIONS

Database CAPLUS on STN, Acc. No. 1995:995241, Gozzini et al., WO 9525763 A1 (Sep. 28, 1995) (abstract).*

* cited by examiner

*Primary Examiner* — Brian J Davis

(57) ABSTRACT

In another exemplary embodiment, an amine functional curing agent has an Amine Hydrogen Functionality (AHF) of at least 7 and an Amine-Hydrogen Equivalent Weight (AHEW) of at least about 50.

6 Claims, No Drawings

HIGH FUNCTIONALITY AMINE COMPOUNDS AND USES THEREFOR

CROSS-REFERENCE TO RELATED APPLICATIONS

This application is the National Phase of International Application PCT/US2008/056947 filed Mar. 14, 2008 which designated the U.S. and which claims priority to U.S. Provisional App. Ser. No. 60/895,060 filed Mar. 15, 2007. The noted applications are incorporated herein by reference.

FIELD OF THE DISCLOSURE

This disclosure, in general, relates to amine compounds useful as curing agents.

BACKGROUND

Manufacturing processes commonly used in conjunction with the production of epoxies include filament winding, pultrusion, infusion molding, resin transfer molding (RTM), vacuum assisted RTM (VARTM), and wet lay-up or vacuum bag techniques.

Polyoxyalkylene amines, or "polyetheramines" as they are sometimes called, are useful as curing agents in epoxy systems to improve flexibility, and to lengthen working time in the manufacture of fiber-reinforced composites. The "working time" is defined as the time period between when the reactive components of the epoxy resin are first mixed with one another and when the mixture is no longer suitable for processing. During the working time, the resin or article containing the resin remains in a pourable, flexible, pliable or otherwise moldable form.

Lower functionality polyetheramines, such as those based on diols and triols, and including commercial products such as the JEFFAMINE® brand amines, have been utilized as epoxy curing agents. Increasing the molecular weight of these lower functional amines yields lower glass transition temperatures (Tg) when used to polymerize standard, liquid epoxy resins, such as those predominantly containing the diglycidyl ether of bisphenol A. Increasing the molecular weight of lower functionality polyetheramines also leads towards undesirably long gel times and related problems such as the reaction of the amines with carbon dioxide and water in the case of surfaces exposed to the atmosphere during curing. The oily surface phenomenon that results from this exposure is often referred to as "amine blushing."

On the other hand, high functionality, lower molecular weight amines have shortened gel times and higher exotherm temperatures because of the higher concentration of reactive groups. Often, higher exotherm temperatures limit the cross-sectional thicknesses of parts that may be molded due to the onset of thermal degradation within the thick sections. Such thermal degradation may be manifested as charring or may result in undesirable mechanical properties.

SUMMARY

In a particular embodiment, an amine composition has the structure:

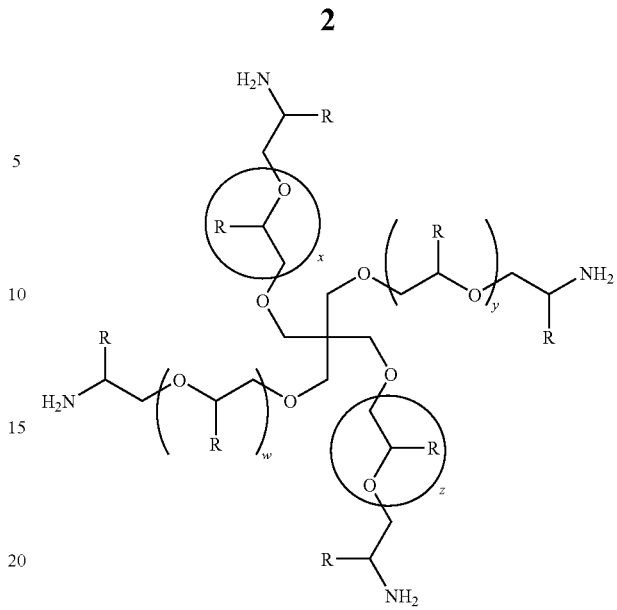

wherein, on average, $0.0 \leq w+x+y+z \leq 25$, and wherein each R may be independently selected from the group consisting of hydrogen, methyl, ethyl, propyl, and butyl.

In another exemplary embodiment, an amine functional curing agent has an Amine Hydrogen Functionality (AHF) of at least 7 and an Amine-Hydrogen Equivalent Weight (AHEW) of at least about 50.

In a further exemplary embodiment, an amine functional curing agent has an Amine Hydrogen Functionality (AHF) of at least 5 and an Amine-Hydrogen Equivalent Weight (AHEW) of at least about 115 and not greater than about 400.

In an additional embodiment, an amine functional curing agent has an Amine Hydrogen Functionality (AHF) of at least 5 and a Molecular Weight (MW) of at least about 700 and not greater than about 2900.

In another exemplary embodiment, an amine functional curing agent has an Amine Hydrogen Functionality (AHF) of at least 5 and an Average Molecular Weight (AMW) conforming to the formulas: $AMW \geq 2000 - 222 \cdot AHF$ and $AMW \leq 500 \cdot AHF$.

In a further exemplary embodiment, an amine functional curing agent has an Amine Hydrogen Functionality of at least 7 and a Molecular Weight (MW) of at least about 700 and not greater than about 5600.

In an additional embodiment, a method of preparing a cured epoxy resin includes providing an amine composition according to any one of the above amine functional curing agents or amine compositions, providing a polyfunctional epoxy resin, and contacting the polyfunctional epoxy resin and the polyamine composition with one another.

In another exemplary embodiment, a method of preparing a polyurea includes providing an organic polyisocyanate, providing an amine composition according to any one of the above amine compositions or the amine functional curing agents, and contacting the organic polyisocyanate and the polyamine composition with one another.

DETAILED DESCRIPTION

In an exemplary embodiment, the disclosure is directed to an amine compound based on a polyol or polyhydric alcohol having at least 4 hydroxyl groups and useful as an epoxy curing agent or a co-reactant for formation of polyurea. In a particular embodiment, the amine compound is based on an alkoxylated pentaerythritol or alkoxylated dipentaerythritol. For example tetrafunctional polyols, such as reaction products of pentaerythritol with oxides of ethylene, propylene, or butylenes may be reductively aminated to provide epoxy curing agents having functionalities of eight and higher. In an example, the amine compound provides desirable reactivity and processing properties, in addition to desirable mechanical properties in a cured product.

In an exemplary embodiment, the amine compound has a high Amine Hydrogen Functionality (AHF). Amine Hydrogen Functionality (AHF) is defined as the sum of the number of hydrogens attached to each primary or secondary amine nitrogen atom in the amine compound. In particular, each primary amine of the amine compound contributes two (2) to the Amine Hydrogen Functionality (AHF), each secondary amine of the amine compound contributes one (1) to the Amine Hydrogen Functionality (AHF), and each tertiary amine of the amine compound contributes zero (0) to the Amine Hydrogen Functionality (AHF). As such, an amine compound including, for example, four primary amine groups has an Amine Hydrogen Functionality (AHF) of 8. In another example, an amine compound having three primary amine groups has an Amine Hydrogen Functionality (AHF) of 6. In a further example, an amine compound having three primary amine groups and a secondary amine group has an Amine Hydrogen Functionality (AHF) of 7. The Amine Hydrogen Functionality (AHF) of the amine compound, for example, may be altered by converting one or more primary amine groups to a secondary amine group.

In a particular embodiment, the amine compound has an Amine Hydrogen Functionality (AHF) of at least 5. More particularly, the amine compound may have an Amine Hydrogen Functionality (AHF) of at least 6, such as at least 7, or even at least 8. In an exemplary embodiment, the Amine Hydrogen Functionality (AHF) is not greater than 14, such as not greater than 13.

The amine compound may be further characterized by Amine-Hydrogen Equivalent Weight (AHEW). The Amine-Hydrogen Equivalent Weight (AHEW) is defined as the average molecular weight of the amine compound divided by the Amine Hydrogen Functionality (AHF). In an exemplary embodiment, the Amine-Hydrogen Equivalent Weight (AHEW) may be at least about 50, such as at least about 70, at least about 115, or even at least about 120. In a further example, the Amine-Hydrogen Equivalent Weight (AHEW) may be not greater than about 400. For example, the Amine-Hydrogen Equivalent Weight (AHEW) may be not greater than about 350, such as not greater than about 300, not greater than about 200, or even not greater than about 150. In particular, the amine compound may have an Amine-Hydrogen Equivalent Weight (AHEW) in a range of about 50 to about 400, such as a range of about 115 to about 400, or even a range of about 115 to about 150. In particular, the amine compound has a functionality of five or higher and has an AHEW of at least 50.

Further, the amine compound may have an average molecular weight of at least about 600, such as at least about 670, at least about 700, or even at least about 800. The average molecular weight of the amine compound may be not greater than about 5600. For example, the average molecular weight may be not greater than about 4800, such as not greater than about 2900, not greater than about 2000, or even not greater than about 1500. In particular, the average molecular weight may be in a range of about 600 to about 5600, such as about 700 to about 4800, or even about 800 to about 1500.

In particular, the desired average molecular weight may be, at least in part, related to the Amine Hydrogen Functionality (AHF) for various applications. In a particular embodiment, the desirable average molecular weight (AMW) of the amine compound is a function of the Amine Hydrogen Functionality (AHF). For example, the AMW of the amine compound may be bounded on the lower side by the equations: $AMW \geq 2000 - 222 \cdot AHF$ and $AMW \geq 0$. In another example, the AMW of the amine compound may be bounded on the high side by the equation: $AMW < 400 \cdot AHF$.

To vary the AHEW of the amine to be formed from the multi-functional starting material, one may adjust the molecular weight of the starting polyol by controlling the addition of oxides (e.g., ethylene oxide, propylene oxide, or butylene oxide). Termination of the polyol chains by the reaction of butylene oxide may lead to greater steric hindrance of the amine in the final product. As such, the reactivity of amines prepared from such starting materials is significantly lower than that of amines obtained when propylene oxide is used to terminate the ends of the polyol starting material. The use of ethylene oxide to terminate the ends, leads to even less steric hindrance, and therefore greater reactivity of the final amine. Additionally, the greater reactivity of the amine formed from the ethylene oxide capped polyol leads to partial condensation of such amines during the amination process, thus leading to even higher functionality than might normally be realized from the starting material. In an example, partially capping the starting polyol with ethylene oxide may be used as a strategy to increase the average molecular functionality of the hardener, while still yielding a slower reacting hardener once the selected amount of coupling has reached completion.

In a particular example, the amine compound is formed from alkoxylated polyol compounds, wherein the polyol compound has at least about 4 hydroxyl groups. An example of a polyol that might be used as starting material to form the amine compound includes erythritol, pentaerythritol, di-pentaerythritol, and their alkoxylates, either alone or in admixture with one another. Alternatively, a high-functionality polyol may be used, such as, Mannich polyol, amine polyol, sucrose/glycol polyol, sucrose/glycerine polyol, sucrose/amine polyol, sorbitol polyol, or any combination thereof.

The polyol may be alkoxylated to increase molecular weight and thus, manipulate the Amine-Hydrogen Equivalent Weight (AHEW) of the final amine. For example, the polyol or alkoxylates thereof may be alkoxylated with ethylene oxide, propylene oxide, butylene oxide, or any combination thereof. In particular, sequential alkoxylation using different species may provide desirable properties in the final amine compound. For example, alkoxylation using ethylene oxide or propylene oxide followed by alkoxylation using butylene oxide may provide steric hindrance that influences the reactivity of the amine compound produced from these polyols. In another example, sequentially alkoxylating with propylene oxide followed by alkoxylating with ethylene oxide may increase the reactivity of the final amine compound. Alkoxylation conditions may include contacting an alcohol initiator with an oxide and a catalyst at a temperature range of 90-160° C. and pressure range of 40-100 psi, for a time sufficient for the oxide to react.

The alcohol groups in the alkoxylated polyol may be converted to amine through reductive amination. For example, the polyol may be reductively aminated in the presence of hydrogen and excess ammonia. Particular processes conditions include contacting the polyol with excess ammonia and hydrogen and a suitable amination catalyst at pressure in the range 1200-2500 psi, temperatures in the range 180-240° C., for an appropriate time to give high conversion to amine.

In a particular embodiment, the amine compound is based on alkoxylated pentaerythritol and has the general formula (I):

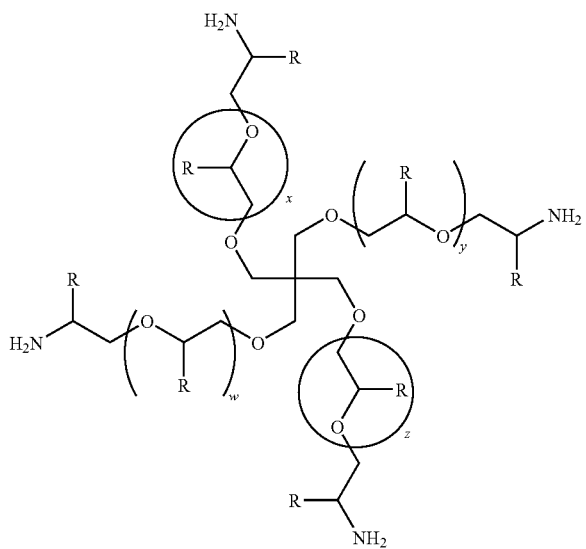

wherein, on average, $0.0 \leq w+x+y+z \leq 25.0$, and wherein each R may be independently selected from the group consisting of hydrogen, methyl, ethyl, propyl, and butyl.

For example, the sum of w, x, y, and z may be in a range between 4.0 and 13.0, such as a range between 4.0 and 10.0. In a particular example, the sum of w, x, y, and z may be in a range between 4.0 and 5.0. In another example, the sum of w, x, y, and z may be in a range between 8.0 and 9.0.

In a particular embodiment, selection of R groups proximate to the amine groups influences the reactivity of the amines. For example, an ethyl, propyl or butyl group may provide steric hindrance that results in reduced reactivity. In contrast, use of a hydrogen in place of R may provide increased reactivity.

The amine compound of formula (I) may have at least one primary amine, such as at least two primary amines, at least three primary amines, or even, at least four primary amines. Alternatively, one or more of the amines may be converted to secondary amines.

The amine compound of formula (I) may have an average molecular weight of at least about 600, such as at least about 800. Further the amine compound may have an Amine-Hydrogen Equivalent Weight (AHEW) of at least about 50, such as at least about 70, or even at least about 115.

In addition to the use of the polyamines described above, the above amines may be combined with one another, with amines of the prior art, or any combination thereof, to form an amine composition. An amine useful in combination includes, for example: N-aminoethylpiperazine ("AEP"); diethylenetriamine ("DETA"); triethylenetetramine ("TETA"); tetraethylenepentamine ("TEPA"); 2-methylpentamethylene diamine (Dytek® A—DuPont); 1,3-pentanediamine (commercially available from Invista North America S.A.R.L. Corporation under the mark DYTEK®EP, DYTEK is a registered mark of Invista North America S.A.R.L. Corporation); trimethylhexamethylene diamine (1:1 mix of 2,2,4-, and 2,4,4-isomers is commercially available under the mark VESTAMIN® TMD—VESTAMIN is a registered mark of Evonik Industries AG); polyamide hardeners; polyamidoamine hardeners; Mannich-base type hardeners; bis (aminomethyl)cyclohexylamine ("1,3-BAC"); isophorone diamine ("IPDA"); menthane diamine; bis(p-aminocyclohexyl)methane ("PACM"); 2,2'-dimethyl bis(p-aminocyclohexyl)methane ("DMDC"); dimethyldicyclohexylmethane); 1,2-diaminocyclohexane; 1,4-diaminocyclohexane; meta-xylene diamine ("m-XDA"); norbornanediamine ("NBDA"); meta-phenylene diamine ("m-PDA"); diaminodiphenylsulfone ("DDS" or "DADS"); methylene dianiline ("MDA"); JEFFAMINE® D-230 amine (Huntsman); JEFFAMINE® D-400 amine (Huntsman); JEFFAMINE® T-403 amine (Huntsman); diethyltoluenediamine ("DETDA"), or any combination thereof.

The amines, combinations, and processes provided herein are particularly beneficial in providing epoxy systems having desirable cure time and desirable process characteristics, such as low viscosity.

The amine compound may be reacted with an epoxy resin to form a cured epoxy resin. Suitable polyfunctional epoxy resins include those which have at least two epoxy end groups and include the following:

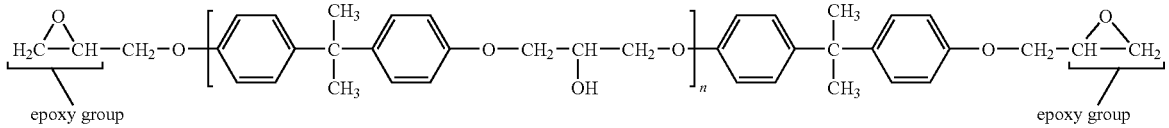

in which n may be between 0 and about 4; DGEBF (diglycidylether of bisphenol F) having the following structure:

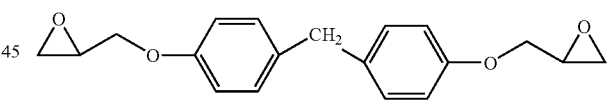

such as ARALDITE® GY 285 epoxy from Huntsman; and tri- and higher functional epoxy resins such as TACTIX® 742 epoxy from Huntsman:

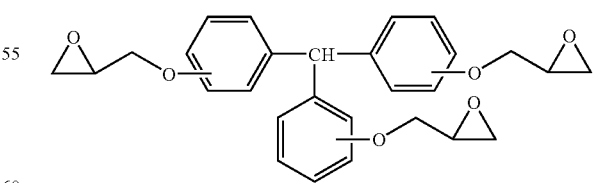

Epoxy functional novolac resins such as D.E.N.® 438 epoxy resin, ARALDITE® EPN 1180 epoxy resin, D.E.N.® 431 epoxy resin, are also suitable for use in the process. D.E.N. is a registered mark of The Dow Chemical Company and ARALDITE is a registered mark of the Huntsman Corporation. All materials which contain at least two epoxy groups in their molecular structure are suitable, including without limitation those described above, and such materials are conveniently referred to as "polyfunctional epoxy resin."

In another embodiment, an amine can be reacted with an organic polyisocyanate to form a polyurea. These polyisocyanates include standard isocyanate compositions, such as MDI-based quasi prepolymers, such as those available commercially as RUBINATE® 9480, RUBINATE® 9484, and RUBINATE® 9495 from Huntsman Corp. Liquified MDI, such as MONDUR® ML, may be used as all or part of the isocyanate. Exemplary isocyanates can include aliphatic isocyanates of the type described in U.S. Pat. No. 4,748,192. Accordingly, they include typically aliphatic diisocyanates and, more particularly, include the trimerized or the biuretic form of an aliphatic diisocyanate, such as hexamethylene diisocyanate, or the bifunctional monomer of the tetraalkyl xylene diisocyanate, such as the tetramethyl xylene diisocyanate. Cyclohexane diisocyanate is also to be considered a preferred aliphatic isocyanate. Other useful aliphatic polyisocyanates are described in U.S. Pat. No. 4,705,814 which is fully incorporated herein by reference thereto. They include aliphatic diisocyanates, for example, alkylene diisocyanates with 4 to 12 carbon atoms in the alkylene radical, such as 1,12-dodecane diisocyanate and 1,4-tetramethylene diisocyanate. Also described are cycloaliphatic diisocyanates, such as 1,3 and 1,4-cyclohexane diisocyanate as well as any desired mixture of these isomers, 1-isocyanato-3,3,5-trimethyl-5-isocyanato methylcyclohexane (isophorone diisocyanate); 4,4'-,2,2'- and 2,4'-dicyclohexylmethane diisocyanate as well as the corresponding isomer mixtures, and the like. Further, a wide variety of aromatic polyisocyanates may be used to form a foamed polyurea elastomer. Typical aromatic polyisocyanates include p-phenylene diisocyanate, polymethylene polyphenylisocyanate, 2,6-toluene diisocyanate, dianisidine diisocyanate, bitolylene diisocyanate, naphthalene-1,4-diisocyanate, bis(4-isocyanatophenyl)methane, bis(3-methyl-3-iso-cyanatophenypmethane, bis(3-methyl-4-isocyanatophenyl)methane, and 4,4'-diphenylpropane diisocyanate. Other aromatic polyisocyanates of use are methylene-bridged polyphenyl polyisocyanate mixtures which have a functionality of from about 2 to about 4. These latter isocyanate compounds are generally produced by the phosgenation of corresponding methylene bridged polyphenyl polyamines, which are conventionally produced by the reaction of formaldehyde and primary aromatic amines, such as aniline, in the presence of hydrochloric acid and/or other acidic catalysts. Processes for preparing polyamines and corresponding methylene-bridged polyphenyl polyisocyanates therefrom are described in the literature and in many patents, for example, U.S. Pat. Nos. 2,683,730; 2,950,263; 3,012,008; 3,344,162 and 3,362,979, all of which are fully incorporated herein by reference thereto. Usually, methylene-bridged polyphenyl polyisocyanate mixtures contain about 20 to about 100 weight percent methylene diphenyldiisocyanate isomers, with the remainder being polymethylene polyphenyl diisocyanates having higher functionalities and higher molecular weights. Typical of these are polyphenyl polyisocyanate mixtures containing about 20 to about 100 weight percent diphenyldiisocyanate isomers, of which about 20 to about 95 weight percent thereof is the 4,4'-isomer with the remainder being polymethylene polyphenyl polyisocyanates of higher molecular weight and functionality that have an average functionality of from about 2.1 to about 3.5. These isocyanate mixtures are known, commercially available materials and can be prepared by the process described in U.S. Pat. No. 3,362,979. A preferred aromatic polyisocyanate is methylene bis(4-phenylisocyanate) or "MDI". Pure MDI, quasi-prepolymers of MDI, modified pure MDI, etc. are useful to prepare a polyurea. Since pure MDI is a solid and, thus, often inconvenient to use, liquid products based on MDI or methylene bis(4-phenylisocyanate) are used herein. U.S. Pat. No. 3,394,164, incorporated herein by reference thereto, describes a liquid MDI product. More generally, uretonimine modified pure MDI is included also. This product is made by heating pure distilled MDI in the presence of a catalyst. The liquid product is a mixture of pure MDI and modified MDI. The term isocyanate also includes quasi-prepolymers of isocyanates or polyisocyanates with active hydrogen containing materials. "Organic di-isocyanate" may include the foregoing isocyanates.

In particular, embodiments of the amine compounds, amine compositions, and method thereof provide desirable technical advantages. For epoxy hardeners containing primary amines, having a higher AHEW generally results in a lower concentration of amine groups (and also epoxide groups) in the final epoxy formulation of a given stoichiometry. This is a performance advantage in epoxy coatings formulations because a lower concentration of amine groups of the surface of epoxy coatings can result in less sorption of contaminants from the air, such as carbon dioxide or moisture. A harmful phenomenon, known as "amine blush", can be reduced or eliminated from the surfaces of amine-cured epoxy coating formulations by reducing the amount of carbon dioxide and moisture pick-up during air exposure. Higher AHEW alone may not reduce the tendency to form amine blush if the gel time of the formulation is extended. This is believed to be due to the longer contact time between the air and a mobile, amine containing formulation prior to reaction of the amine with epoxide. However, coupling high AHEW with high functionality in the same compound may promote earlier gelation of the system, thus immobilizing it and limiting the amount of blushing that may occur. Thus, hardeners based upon amination of polyols having a functionality of four or greater, particularly those based on pentaerythritol derivatives, may provide particular advantages when used to form network polymers.

In particular, using the amine compounds limits the concentration of amine groups in the curable epoxy formulation while promoting gelation of the system at relatively low extents of reaction. This provides benefits of lower exotherm temperatures in molded parts having thick sections and less likelihood of the various problems related to amine blush formation on surfaces exposed to the air during curing, including reduced photo-yellowing. In particular, slow enough reactivity of end groups that gel times occur at relatively low conversion, yet exothermic heats of reaction are moderate, allows greater latitude of formulation.

Of forty-three aliphatic amine compounds commonly used with epoxy resins, only six had average AHF greater than four. The non-adduct hardeners of highest functionality (six) were polyalkylene etheramines (viz. JEFFAMINE® T-403 amine, JEFFAMINE® T-3000 amine, and JEFFAMINE® T-5000 amine, all from Huntsman Corp.). The only hardeners having species present with functionality greater than six were a high viscosity amine-epoxy adduct (as described further below) and tetraethylenepentamine (TEPA) which has a relatively low AHEW of about 30 and a very high reactivity due to the combination of low AHEW and high functionality.

In contrast to high-functionality, low AHEW, aliphatic amine systems, an advantage of high-functionality amines of sufficient molecular weight (and therefore AHEW), based on alkoxylates of multifunctional starting materials like pentaerythritol, di-pentaerythritol, etc. is that they can provide moderate, even slow, reactivity and long working times, despite their high functionality. In epoxy resin formulations, other advantages of using amines characterized by both high functionality coupled with high AHEW is that with standard liquid epoxy resins, such as diglycidyl ether of bisphenol A type resins having epoxide equivalent weights (EEWs) of about 180 to 200, their mix ratio and viscosity ratio are more closely matched, allowing for easier mixing and a more even distribution of fillers between both parts of the two part systems, prior to mixing.

Yet another advantage of amine hardeners showing a combination of high functionality coupled with high AHEW is that, although such amines of relatively high AHEW might be expected to yield a relatively low glass transition temperature (Tg) in the cured product, the high functionality increases crosslinking, thus raising the Tg of the cured polymer.

The amine compounds described above generally have a combination of high amine hydrogen functionality (typically six or greater) and relatively high AHEW value that is not found among the currently available epoxy curing agents, apart from epoxy amine adducts. Epoxy amine adducts are amine blends that result from the reaction of a significant stoichiometric excess of amine with an epoxy resin such that the blend remains ungelled. Although epoxy amine adducts are widely utilized by formulators as a means of reducing amine blushing problems, there are disadvantages to their use. Among the disadvantages of epoxy amine adducts as a means of simultaneously obtaining high-functionality and high AHEW are:

1) Such adducts contain numerous hydroxyl groups that greatly increase their viscosity and decrease ease of mixing into and subsequent degassing of the epoxy formulation.

2) To avoid excessively high molecular weight due to coupling of the adduct molecules during synthesis, excess amine is used which then decreases the AHEW of the adduct blend, or else it is stripped from the mixture using additional processing steps.

3) The amine concentration of the final polymer is not decreased, meaning sorption of atmospheric moisture and carbon dioxide similar to that of lower AHEW materials may occur.

4) The adduction reaction is an additional synthesis step, thus adding complexity to the process and expense to the product.

In a particular embodiment, the amine composition does not include epoxy amine adducts.

EXAMPLES

Two different amine compounds based on pentaerythritol alkoxylates are prepared and are used to polymerize a standard liquid epoxy resin based upon Bisphenol A, having an epoxide equivalent weight of about 184. The aminations are performed using standard methods.

Example 1

Epoxy Resin Curing Using an Amine Based on Pentaerythritol Alkoxylated with 8.5 Moles of Propylene Oxide Based upon wet lab analysis of this amine, the amine has an AHEW of about 85.9 g per amine-hydrogen equivalent. The AHF of the amine, with respect to epoxy curing, is eight.

A casting is made by mixing 89.11 parts of the product of Example 1 with 190.89 parts of epoxy resin of a liquid bisphenol A based epoxy resin (epoxide equivalent weight of 184) and baking it for 3 hours at 80° C. followed by 2 hours at 125° C. in a glass mold to form an unfilled casting with a nominal thickness of one eighth inch. The Tg of this polymer is 98.6° C., when measured via DSC (differential scanning calorimetry) at a heating rate of 20° C. per minute. Mechanical testing shows a flexural strength of 20,600 psi, a tensile strength of 10,200 psi, and a tensile modulus of 446,000 psi.

Example 2

Epoxy Resin Curing Using an Amine Based on Pentaerythritol Alkoxylated with 8.5 Moles of Propylene Oxide Followed by 5 moles of Butylene Oxide Based upon wet lab analysis of this amine, the amine has an AHEW of about 126 g per amine-hydrogen equivalent. The AHF of the amine, with respect to epoxy curing, is eight.

A casting is made by mixing 106.76 parts of this amine, at a 1:1 stoichiometry with 173.24 parts of epoxy resin of a liquid bisphenol A based epoxy resin (epoxide equivalent weight of 184) and baking it for 2 hours at 110° C. followed by 2 hours at 125° C. to form an unfilled casting with a nominal thickness of one eighth inch. The glass transition temperature (Tg) of this polymer is 64° C., when measured via DSC (differential scanning calorimetry) at a heating rate of 20° C. per minute.

In contrast, when JEFFAMINE® D-400 amine, such amine having an AHEW of 115 and an AHF of 4, is used at a 1:1 stoichiometry level of 56 parts to cure 100 parts of epoxy resin of a liquid bisphenol A based epoxy resin (epoxide equivalent weight of 184), the resultant Tg is 56° C., even though the AHEW of the amine was slightly lower.

Mechanical testing shows the pentaerythritol-based amine, when used to polymerize a standard, bisphenol A based, liquid epoxy resin, gives a product having a flexural strength of 17,900 psi, a tensile strength of 7200 psi and a tensile modulus of 467,000 psi.

What is claimed is:
1. An amine composition having the structure:

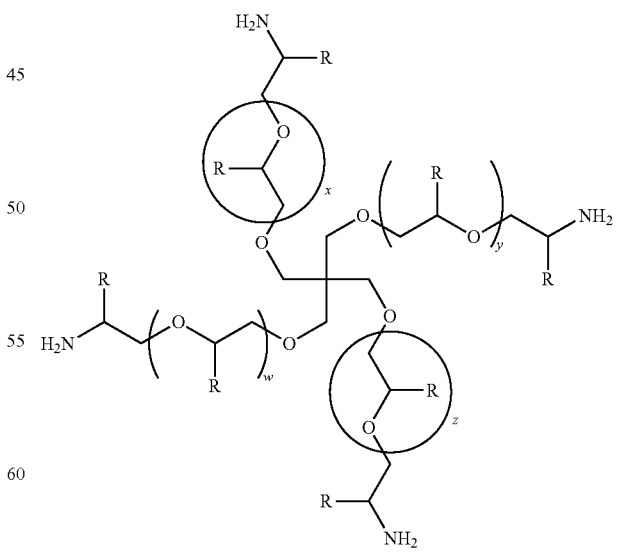

wherein, on average, $0.0 \leq w+x+y+z \leq 25.0$, wherein each R is selected from the group consisting of hydrogen, methyl, ethyl, propyl, and butyl, and wherein the amine composition has an Amine-Hydrogen Equivalent Weight (AHEW) of at least about 70.

2. The amine composition of claim 1, wherein, on average, $4.0 \leq w+x+y+z \leq 5.0$.

3. The amine composition of claim 1, wherein, on average, $8.0 \leq w+x+y+z \leq 9.0$.

4. The amine composition of claim 1, wherein R is hydrogen.

5. The amine composition of claim 1, wherein R is methyl.

6. The amine composition of claim 1, wherein R is ethyl.

* * * * *